United States Patent [19]

De et al.

[11] Patent Number: 4,902,961
[45] Date of Patent: Feb. 20, 1990

[54] MICROWAVE SYSTEM FOR MONITORING WATER CONTENT IN A PETROLEUM PIPELINE

[75] Inventors: Bibhas R. De, Laguna Beach; Paul L. Donoho, Fullerton; David E. Revus, Yorba Linda; Russell E. Boyer, Fullerton, all of Calif.

[73] Assignee: Chevron Research Company, San Francisco, Calif.

[21] Appl. No.: 35,838

[22] Filed: Apr. 8, 1987

[51] Int. Cl.$^4$ .............................................. G01N 22/00
[52] U.S. Cl. ................................. 324/640; 73/61.1 R; 73/73; 324/637
[58] Field of Search ............. 324/58 A, 58.5 A, 58 R, 324/58.5 R, 58 C, 58.5 C; 73/61.1 R, 73, 64

[56] References Cited

U.S. PATENT DOCUMENTS

| | | |
|---|---|---|
| 2,659,860 | 11/1953 | Breazeale ........................ 324/58.5 A |
| 3,196,385 | 7/1965 | Vestergaard et al. ............. 324/58.5 |
| 3,586,971 | 6/1971 | Bosisio ............................. 324/58.5 C |
| 3,644,826 | 2/1972 | Cornetet, Jr. ..................... 324/58.5 |
| 3,811,087 | 5/1974 | Schmelzer ........................ 324/58.5 A |
| 3,818,333 | 6/1974 | Walker ............................. 324/58.5 A |
| 4,074,184 | 2/1978 | Dechene et al. ................ 324/434 X |
| 4,107,993 | 3/1978 | Shuff et al. ...................... 73/290 |
| 4,167,736 | 9/1979 | Tomlinson ....................... 343/5 NA |
| 4,240,028 | 12/1980 | Davis, Jr. ......................... 324/61 R |
| 4,289,020 | 9/1981 | Paap ................................. 73/61.1 R |
| 4,301,400 | 11/1981 | Paap ................................. 324/58.5 |
| 4,352,288 | 10/1982 | Paap et al. ....................... 73/61 R |
| 4,381,485 | 4/1983 | Steinbrecher .................... 324/58 |
| 4,423,623 | 1/1984 | Ho et al. .......................... 73/61 |
| 4,486,714 | 12/1984 | Davis, Jr. et al. ................. 324/376 |
| 4,490,676 | 12/1984 | Davis, Jr. et al. ................. 324/376 |
| 4,503,384 | 3/1985 | Nagy et al. ....................... 324/61 |
| 4,519,982 | 5/1985 | Davis, Jr. et al. ................. 422/68 |
| 4,543,821 | 10/1985 | Davis, Jr. ......................... 73/153 |
| 4,651,085 | 3/1987 | Sakurai et al. ................... 324/58.5 R |
| 4,727,311 | 2/1988 | Walker ............................. 324/58.5 A |

OTHER PUBLICATIONS

L. A. Davis, Jr., "VHF Electrical Measurement of Saturations in Laboratory Floods" (SPE 8847), Apr. 20–23, 1980.

Primary Examiner—Reinhard J. Eisenzopf
Assistant Examiner—Robert W. Mueller
Attorney, Agent, or Firm—Edward J. Keeling

[57] ABSTRACT

A method and apparatus for determining the water content of crude oil in a pipeline is disclosed. The device consists of S-band tarnsmitting and receiving antennas, and X-band transmitting and receiving antennas. These are used to determine the complex dielectric constant of the fluid in a pipeline. Water salinity and an adjustment to the mixing formula are calculated using X-band and S-band sidewall links. The overall water content of the pipeline can then be determined by using as S-band main link that transmits a wave through a representative portion of the entire pipeline.

12 Claims, 1 Drawing Sheet

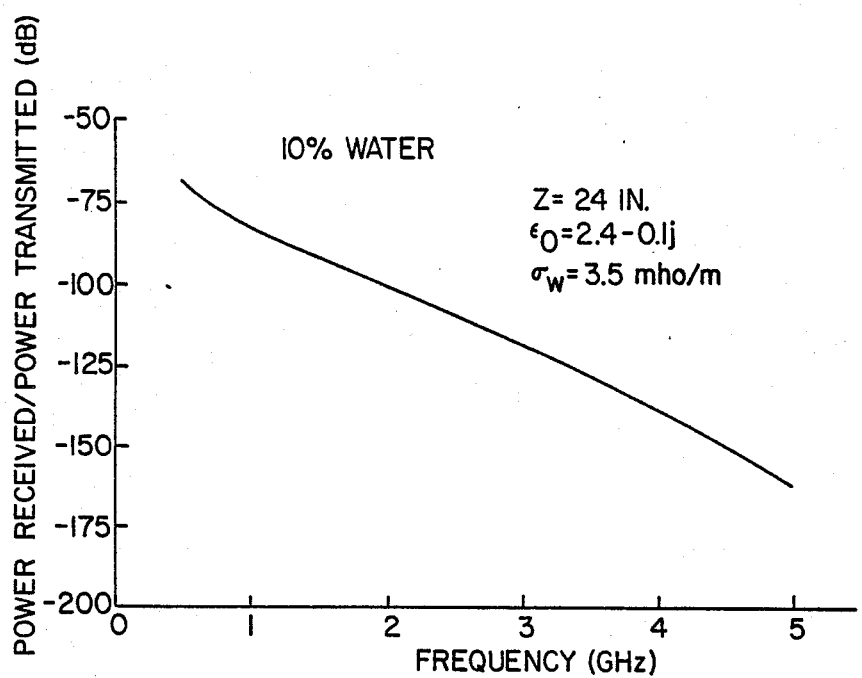
FIG._1.
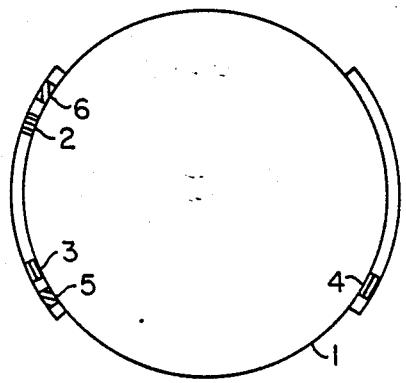
FIG._2.
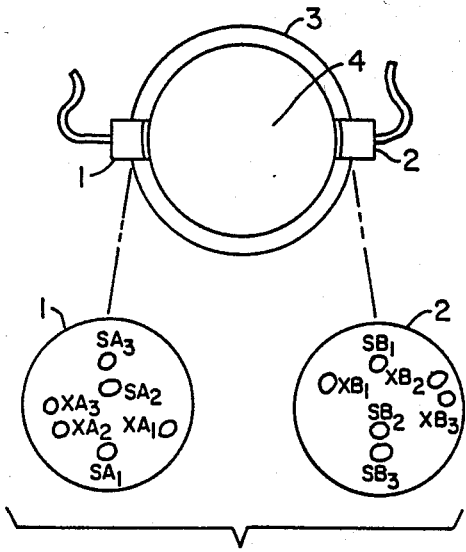
FIG._3.

MICROWAVE SYSTEM FOR MONITORING WATER CONTENT IN A PETROLEUM PIPELINE

FIELD OF THE INVENTION

The present invention relates to the field of two-phase measurement. More specifically, the present invention relates to measurement of the water content of petroleum in a petroleum pipeline. It can also be applied to multi-phase measurement of other material.

BACKGROUND OF THE INVENTION

Crude oil produced from subterranean wells is frequently contaminated with undesirable materials. The most common of these materials is water. The fluid produced from an oil well can contain anywhere from less than 1% water to 99% water or more. Produced fluids containing these high "water cuts" are treated to remove most or all of the water because crude oil sales contracts typically allow a maximum of 1 to 3% water.

After treatment, the crude oil stream is monitored to determine the amount of water remaining in the crude. Various methods of monitoring the water content of a crude oil stream have been proposed. For example, U.S. Pat. No. 4,596,136 describes a system in which a sample of oil is removed. This system (and all others which require the removal of a sample) assume that the water content of the sample is representative of the water content of the entire flow stream. This is frequently not a valid assumption, particularly in large pipelines which contain significant concentrations of water.

Other methods have also been proposed. For example, spinners, venturies, or capacitance probes have been used to determine the water content of crude oil. Among other disadvantages, all of these systems require the insertion of one or more devices into the crude oil stream. These intrusive systems can significantly increase the pressure drop in a pipeline, requiring additional pumping capacity. Many of these devices also assume that the conditions in one portion of the pipeline are representative of the entire pipeline. This again may not be the case.

In summary, there is a need to provide a method and means for determining the water content of flowing crude oil streams which is highly accurate, nonintrusive, and which does not require the removal of a sample that is representative of the entire crude oil stream.

BRIEF SUMMARY OF THE INVENTION

The present invention provides a nonintrusive method and means for accurately determining the water content of crude oil flowing in a pipeline. The device is comprised of two antenna pots mounted flush in the walls of a petroleum pipeline. In each of the ports are various S- and X-band antennas. These antennas are used to derive the real and imaginary parts of the complex dielectric constant of the oil/water mix ($\epsilon^*$) from which the volume fraction of water ($\phi$) can ultimately be determined.

In the first port is an S-band (or other low frequency) transmitting antenna and in the second port is an S-band receiving antenna. Since an ideal mixing formula for the complex dielectric constant in the low frequency region is not known, the volume fraction of water cannot be calculated directly. Therefore, an "adjustment factor" ($\rho$) must be calculated. In addition, it is necessary to know the conductivity of the water ($\sigma_w$) to calculate $\phi$ when $\epsilon^*$ is known.

The adjustment factor and water conductivity are determined by utilizing a set of low frequency (S-band) and (X-band) transmitting and receiving antennas contained entirely within one of the antenna ports. Across the short distance of the antenna port, the attenuation and the phase shift of a transmitted signal in either the X- or S-band can be determined unambiguously. From the measurments, the value of $\epsilon_s^*$ and $\epsilon_x^*$, i.e., the value of $\epsilon^*$ in the S- and X-band for the mixture near the wall, are determined. Using $\epsilon_x^*$, the value of $\sigma_w$ and the volume content of water near the wall ($\phi$) can also be determined since no adjustment factor to the mixing formula is necessary for X-band radiation. By knowing $\sigma_w$ and $\phi$, the value of the S-band adjustment factor to the mixing law ($\rho$) can be calculated for the near-wall region. Since the S-band adjustment factor to the mixing formula determined at any given time and the dielectric constant of water can be assumed to be constant throughout the volume of the pipe, these values of $\rho$ and $\sigma_w$ can also be applied to the S-band link across the pipe. While it is not possible to unambiguously measure the phase shift in the S-band link across the pipe, it is possible to calculate it if the distance between the S-band antennas in the wall, and the two ports is known.

The wave attenuation in the S-band link across the pipe is then measured, making it possible to determine the overall volume fraction of water contained within the pipe ($\phi$) in the region between the antenna ports.

The apparatus for carrying out the above calculations consists of a first antenna port mounted flush in a wall of the pipeline, the first antenna port contains an X-band link and a sidewall S-band link. The X-band link consists of an X-band transmitting antenna and an X-band receiving antenna located within one-half of the minimum expected effective wavelength of the X-band radiation. The sidewall S-band link consists of a sidewall S-band transmitting antenna and a sidewall S-band receiving antenna located likewise within one-half of thewavelength of the S-band radiation. A main link S-band transmitting antenna is also included in the first antenna port.

A second antenna port is mounted flush in the wall of the pipeline substantially diametrically opposite the first antenna port. The second antenna port contains a main link S-band receiving antenna. The device also includes a means for generating waves, a means for measuring phase shift, and attenuation of a signal transmitted through the X-band link, a means for measuring phase shift and attenuation of a signal transmitted through said sidewall S-band link, and a means for measuring attenuation of a signal transmitted from the main link S-band transmitting antenna to the main link S-band receiving antenna.

Duplicates of the above antennas may be provided to increase the accuracy of the device. For example, the sidewall X-band link may comprise an X-band transmitting antenna and two X-band receiving antennas. Similarly, the S-band links may comprise a single transmitting and two receiving antennas. Further, the second antenna port may be similarly arranged to the first antenna port. When the first antenna port transmits in the S-band link, the second antenna port receives and vice versa. It is also possible to provide two sets of the antenna ports along horizontal and vertical diameters of the pipe to detect and quantify gravitational settling.

Unlike the prior art, in utilizing the above approach it is not necessary to assume that the overall water content of the oil in the pipe is represented by an individual portion of the pipe since a bulk volume fraction water will be found. Further, it is unnecessary to insert a device into the flowing stream of oil which would not only increase the pressure drop in the pipeline, but can also result in disturbances to the flow stream at the point of measurement that will result in measurement inaccuracies.

BRIEF DESCRIPTION OF THE DRAWINGS

FIG. 1 shows the ratio of power received to power transmitted for various frequency signals.

FIG. 2 illustrates schematically the manner in which the described invention is operated.

FIG. 3 shows the anticipated antenna configuration in the preferred embodiment. The antenna ports are shown in the pipeline in cross-section and in enlarged front views.

DESCRIPTION OF THE PREFERRED EMBODIMENTS

In the discussion below it is not necessary to assume that the distribution of water over a cross section of a pipeline is uniform. It is, however, necessary to assume that the distribution of water conductivity is uniform over the cross section of the pipeline. In almost all cases this will be a valid assumption. It is also necessary to assume that the adjustment to the mixing formula for high frequency radiation is the same near the wall as it is throughout the pipe. This will generally be a valid assumption if the *shape* of the water droplets is substantially the same throughout the pipe because droplet shape largely determines $\rho$.

By transmitting electromagnetic waves some distance through a fluid medium (flowing or not), it is well known that two parameters of the medium may be measured:

$\alpha$ = phase shift of the wave (radians/meter)
$\beta$ = attenuation of the wave (neper/meter)

From these two parameters it is also well known that the real and imaginary parts of the complex dielectric constant ($\epsilon^*$) can be described as follows:

$$\epsilon^* = \epsilon' - i\epsilon'' \quad (1)$$

$$\epsilon' = \frac{\alpha^2 - \beta^2}{\mu\omega^2} \quad (2)$$

$$\epsilon'' = \frac{2\alpha\beta}{\mu\omega^2} \quad (3)$$

where:
$\epsilon'$ = the real part of the complex dielectric constant
$\epsilon''$ = the imaginary part of the complex dielectric constant
$\mu$ = permeability of free space
$\omega$ = the circular frequency of the wave ($=2\pi f$ where f = the frequency of the wave)
i = the imaginary constant ($=\sqrt{-1}$)

When the medium is a two-phase mixture of oil and water, it is useful to find a "mixing formula" that will relate the dielectric constant of oil ($\epsilon_o^*$), the dielectric constant of water ($\epsilon_w^*$), and the dielectric constant of the mixture ($\epsilon^*$) to the volume fraction of water ($\phi$). For higher frequency waves (X-band) the mixing law can be defined as follows:

$$\epsilon_x^* = [(1-\phi)\epsilon_o^{*\frac{1}{2}} + \phi\epsilon_w^{*\frac{1}{2}}]^2 \quad (4)$$

(where the subscript "o" indicates oil, the subscript "w" indicates water, and the subscript "x" indicates the composite dielectric constant for X-band radiation).

For lower frequency waves it is necessary to provide a "correction factor" ($\rho$) to the above equation in order to account for the manner in which the oil is disseminated in the oil (e.g., fine mist, oval shaped drops, streaks, etc.). Although this correction factor could be applied in any of several ways to the above equation, in the preferred embodiment the mixing law for S-band radiation is described as follows:

$$\epsilon_s^* = [(1-\phi)\epsilon_o^{*\frac{1}{2}} + \phi\epsilon_w^{*\rho/2}]^2 \quad (5)$$

(where the subscript "s" indicates the composite dielectric constant for S-band radiation).

It is also known that the dielectric constants for oil and water can be described by the following equations:

$$\epsilon_o^* = a - ib \quad (6)$$

$$\epsilon_w^* = \epsilon_\infty + \frac{\epsilon_s - \epsilon_\infty}{1 + (i\omega\tau)^{1-\nu}} - \frac{i\sigma_w}{\omega} \quad (7)$$

where:
a = real part of the complex dielectric constant for oil
b = imaginary part of the complex dielectric constant for oil
$\sigma_w$ = water conductivity
$\epsilon_\infty$ = dielectric constant for water at infinitely high frequency
$\epsilon_s = C - DT + ET^2$
T = fluid temperature
C, D, E = Constants (See later discussion)
$\tau$ = a time constant related to the dielectric absorption feature for water
$\nu$ = a well known constant (see Shawn et al., *J. Chem. Physics*, vol. 67, p. 2257)

It is desirable to rely on the highest possible frequency radiation in using the device for the following reasons. First, at low frequencies antenna dimensions would become impractically large in relation to the size of a pipeline. Second, at low frequencies unwanted interactions of the radiation with the metallic walls of the pipe set in and, third, at higher frequencies the mixing formula is relatively easily defined, [e.g., by equation (5) above].

The upper bound of the frequency is limited by the power ratio which can be practically measured. With a high quality preamplifier, the minimum detectable power level at the receiving antenna would be 80 decibels below one milliwatt (dBm). A realistic value of the transmitted power is 10 watts or 40 dBm. Thus, the minimum power ratio is:

$$40 \text{ dBm} - (-80 \text{ dBm}) = 120 \text{ dBm}$$

The ratio of power received ($P_r$) to power transmitted ($P_t$) is:

$$\frac{P_r}{P_t} = \frac{T_c^2 G^2 \lambda^2}{16\pi^2 Z^2} e^{-2\beta Z}$$

where:

Z = the distance between transmitting and receiving points $T_c$ = the power transmission coefficient at the antenna/fluid interface G = the gain of the transmitting or receiving antenna (assumed to be identical)

λ = the effective wavelength in the fluid

FIG. 1 illustrates the minimum power ratio versus frequency for a typical petroleum pipeline by plotting the quantity 10 log ($P_r/P_t$) as a function of frequency when:

Power loss due to antenna/fluid mismatch = −3 dB
Antenna gain = 0 dB
Pipeline diameter = 24 inches
$\epsilon_o$ = 2.4 − i 0.1
$\sigma_w$ = 3.5 mho/m From this graph it can be found that in a typical application, the maximum frequency which can be employed is 3 GHz.

It should be noted, however, that at this frequency it is impossible to (1) measure α across the pipe because this value can only be measured unambiguously when the pipeline diameter is one-half the effective wavelength or less, and (2) measure φ because at this frequency it is necessary to apply an unknown correction factor ρ to the mixing equation.

In order to overcome the above difficulties, the following device/method is employed as schematically illustrated in FIG. 2 (not drawn to scale for illustration purposes).

Two S-band links are installed in a pipeline 1. The first consists of an S-band transmitting antenna 2 and S-band receiving antennas 3 and 7 (the S-band sidewall link) and the second consists of an S-band transmitting antenna 2 and S-band receiving antenna 4 (the S-band main link). The antennas are mounted flush with the pipeline wall in nonmetallic, preferably ceramic, windows. The main link antennas are placed in the pipeline such that a wave passed through the main link will pass through a representative portion of the two-phase fluid contained within it. In addition, an X-band sidewall link consisting of an X-band transmitting antenna 5 and an X-band receiving antenna 6 is installed flush with the pipeline walls.

Initially, S-band transmitting antenna 2 transmits a signal to S-band receiving antenna 3 and X-band transmitting antenna 5 transmits a signal to X-band receiving antenna 6. The phase shift α and attenuation β of both of these waves can be readily and unambiguously determined because of the short distance involved and, therefore, the values of $\epsilon_s^*$ and $\epsilon_x^*$ can be calculated from equations (1), (2), and (3) above. Values of a, b, $\epsilon_\infty$, C, D, E, τ, ν, and T can also be readily determined as follows:

C, D, and E are empirical constants which can be found in R. P. Wharton et al. doc. of Petroleum Engineers, Paper 9267 (1981).

T can be measured continuously in the pipeline with a temperature probe;

$\epsilon_\infty$ can be readily located in standard tables (=4.6);

a and b can be measured in the laboratory or derived from reference tables (since these values will vary only slightly with time and will also vary only slightly from one crude oil to the next). Note that these values are also frequency independent;

τ can also be derived from standard reference tables; and

ν can be determined from standard reference tables, and in any case can be assumed to be very small or approaching 0 (greatly simplifying the calculations). It is assumed here to be 0.014.

With knowledge of these variables, as well as the frequency of the X-band and S-band waves, it is possible to simultaneously solve equations (4) and (5) for $\sigma_w$, ρ, and φ by substituting equations (6) and (7) in for $\epsilon_o$ and $\epsilon_w$ respectively. Note that it is possible to solve these two equations simultaneously to obtain 3 values because $\epsilon_s^*$ and $\epsilon_x^*$ are complex values.

The S-band transmitting antenna 2 now transmits a signal to S-band receiving antenna 4. The phase shift α of this signal cannot be determined unambiguously but can be calculated. First, a trial value of the phase shift, $\alpha_o$, is calculated by multiplying the phase shift in the sidewall link by the ratio:

$$\alpha_o = \frac{\text{Distance from antenna 2 to antenna 6}}{\text{Distance from antenna 2 to antenna 3}}$$

We then add 180° of phase as many times as needed to the measured phase shift α to bring the result closest to $\alpha_o$. This will give the correct value of the main links phase shift (except in the event that the average water saturation is drastically different from the near wall saturation).

The attenuation β of this signal can be easily measured and, therefore, the value of $\epsilon_s^*$ can be calculated across the pipeline with equations (1), (2) and (3). Furthermore, the value of ρ for the sidewall links should be approximately the same as for the main link for the reasons discussed above. Also, as stated above, it is assumed that the conductivity of the water is uniform throughout the pipeline and is assumed to be constant. Therefore, the spatially-averaged water fraction φ across the pipeline can be determined from equation (5).

As stated above, FIG. 2 is a simplified drawing intended to illustrate the operation of the system. The actual antenna configuration of the preferred embodiment is shown in FIG. 3. In the preferred embodiment, multiple transmitting and receiving antennas are provided in both the sidewall and main links. In addition, the first antenna port is duplicated in the second antenna port. This allows accuracy improvement through making sidewall measurements near both the ports and averaging of their values. In addition, if the values differ radically, it will be an indication of asymmetric distribution in the liquid mixture composition.

The device consists of a first antenna port 1 and a second antenna port 2 mounted flush in the sidewall of a pipeline 3 through which a gas-free oil/water mixture 4 is flowing. The first S-band main link transmitter is a two-element array of antennas designated $SA_1$ and $SA_2$. Similarly, the first S-band main link receiver is a two-element array of antennas designated $SB_1$ and $SB_2$. This configuration is used to created narrow, focused beams at transmission and to concentrate energy on the receiving antennas, which are likewise focused in the direction of the transmitting antennas. The power thus received at the second antenna port is compared with the power received at the first antenna port with the antenna designated $SA_3$. By doing so, the effect of mismatch at the antenna/fluid interface is eliminated and we obtain the absolute power loss for the path length that is the difference between the main link path length and the path length from the transmitting antennas $SA_1$, and $SA_2$ to receiving antenna $SA_3$.

Redundant measurements can be made by reversing the role of the antenna ports, i.e., by using $SB_1$ and $SB_2$ as transmitting antennas and $SA_1$ and $SA_2$ as receiving antennas, with $SB_3$ used to eliminate mismatch at the antenna/fluid interface.

The S-band sidewall links consists of antenna $SA_1$ as the transmitter and $SA_2$ and $SA_3$ as the receivers. The power from $SA_1$ is sequentially received by $SA_2$ and $SA_3$, which are spaced at a distance less than one-half of the effective wavelength apart. Upon taking the difference of the two measurements, $\alpha$ and $\beta$ can be determined and hence $\epsilon'$ and $\epsilon''$ for the sidewall region (which in a typical case will be about one inch from the wall). Duplicate measurements are made to obtain greater accuracy by using $SB_1$ as a transmitting antenna and $SB_2$ and $SB_3$ as receiving antennas.

Similarly, the X-band sidewall links consists of antenna $XA_1$, used as a transmitting antenna, and $XA_2$ and $XA_3$ used as receiving antennas. Upon taking the ratio of the two measurements, $\alpha$ and $\beta$ can be determined and, hence, $\epsilon'$ and $\epsilon''$. Again, duplicate measurements are made for accuracy in the opposite sidewall by using $XB_1$ as a transmitting antenna and $XB_2$ and $XB_3$ as receiving antennas.

All of the above-mentioned attenuation measurements will need to be corrected for an inherent attenuation due to well known "geometric spreading" of radiation (also known as space loss). This correction factor can be calculated from theoretical considerations well known to one skilled in the art or may be determined for all fluids in the system in the laboratory with fluids of known dielectric properties such as alcohol and brines.

From the X-band measurements of $\epsilon'$ and $\epsilon''$, we can readily obtain the values of $\phi$ and $\sigma_w$ for the near wall region using equations (1) to (4) and (7). Using these two values and the values of $\epsilon'$ and $\epsilon''$ obtained from the S-band sidewall link, we can calculate the value of $(\rho)$ from equation (5). Knowledge of these values allows calculation of the water fraction across the cross section of pipe.

All of the antennas discussed above are circularly polarized to minimize the effects of stray radiation.

It should be noted that the above system could be fully automated and computerized so as to provide a continuous measurement of the water fraction $\phi$. This would also allow all measurements to be taken in a time period short enough that the water content does not change during the measurement. It should also be noted that by calculating the conductivity of the water that the salinity of the water can also be continuously monitored.

It is to be understood that while the invention has been described above with a great deal of particularity, that it is manifest that many details of construction and the arrangement of the components may be possible without departing from the spirit and scope of the invention.

For example, the above-described device could be used to measure the composition of materials other than water and oil. Further, with a simple extension of the above-described calculations, the device could be used for three or four-phase measurement. Still further, while the invention has been described with reference to X-band and S-band radiation, other frequencies may be optimum for various pipeline sizes and fluid types. Therefore, the invention is not to be limited by the embodiment set forth herein but is to be limited instead by the attached claims, including the full range of equivalency to which each is entitled.

What is claimed is:

1. Apparatus for analyzing a multi-phase liquid comprising:
   pipeline means for containing the liquid;
   a low frequency transmitting antenna substantially in the S-band near a wall of said means for containing a liquid;
   a low frequency receiving antenna substantially in the S-band located within one-half wavelength of said low frequency transmitting antenna;
   means for determining a phase shift of a low frequency wave; and
   means for determining an amplitude change of the low frequency wave.

2. Apparatus as recited in claim 1 further comprising:
   a complementary high frequency transmitting antenna substantially in the X-band located substantially near said low frequency transmitting antenna;
   a first high frequency receiving antenna substantially in the X-band located within one-half wavelength of said high frequency transmitting antenna;
   a second high frequency receiving antenna substantially in the X-band located such that a wave transmitted from said high frequency transmitting antenna to said second high frequency receiving antenna passes through a representative portion of the liquid;
   means for determining a phase shift and an amplitude change of a wave transmitted from said high frequency transmitting antenna and said first high frequency receiving antenna; and
   means for determining an amplitude change of a wave transmitted from said high frequency transmitting antenna to said second high frequency receiving antenna.

3. Apparatus as recited in claim 2 wherein said means for containing a liquid is a petroleum pipeline.

4. Apparatus as recited in claim 3 wherein said antennas are located in ceramic windows flush with the walls of said pipeline.

5. Apparatus as recited in claim 4 further comprising:
   a duplicate first high frequency receiving antenna substantially in the X-band located adjacent said first high frequency receiving antenna;
   a duplicate second high frequency receiving antenna substantially in the X-band located adjacent said second high frequency receiving antenna; and
   a duplicate low frequency receiving antenna substantially in the X-band located adjacent said low frequency receiving antenna.

6. Apparatus for determining the water content of crude oil in a pipeline comprising:
   (A) a first antenna port mounted flush in a wall of the pipeline further comprising:
      (1) an X-band link comprising:
         (a) an X-band transmitting antenna;
         (b) an X-band receiving antenna located with one-half the wavelength of said X-band transmitting antenna;
      (2) a sidewall S-band link comprising:
         (a) a sidewall S-band transmitting antenna;
         (b) a sidewall S-band receiving antennalocated with one-half wavelength of said first S-band transmitting antenna;
      (3) a main link S-band transmitting antenna;

(B) a second antenna port mounted flush in the wall of the pipeline, said second antenna port containing a main link S-band receiving antenna;

(C) means for measuring phase shift and attenuation of a signal transmitted through said X-band link;

(D) means for measuring phase shift and attenuation of a signal transmitted through said sidewall S-band link; and (E) means for measuring attenuation of a signal transmitted from said main link S-band transmitting antenna to said main link S-band receiving antenna.

7. Apparatus as recited in claim 6 further comprising:
(a) a duplicate X-band receiving antenna;
(b) a duplicate sidewall link S-band receiving antenna; and
(c) A duplicate main link S-band receiving antenna.

8. Apparatus as recited in claim 7 further comprising a third and a fourth antenna port located at substantially right angles to said first and second antenna port.

9. A method for determining the relative proportions of two mixed, dielectrically-dissimilar fluids in a container comprising:
(a) transmitting a low frequency wave substantially in the S-band through said fluids;
(b) measuring a phase shift and attenuation of the wave to obtain the complex dielectric constant of the mixed fluids; and
(c) calculating the relative proportions of the mixed fluids.

10. A method for determining the water content of oil in a flowing pipeline comprising:
(a) transmitting a low frequency signal substantially in the S-band between a low frequency transmitting antenna and a low frequency receiving antenna, said antennas located within one-half wave length;
(b) transmitting a first high frequency signal substantially in the S-band between a high frequency transmitting antenna and a high frequency receiving antenna, said antennas located within one-half wavelength of each other and in close proximity to said low frequency transmitting and receiving antennas; and
(c) transmitting a second high frequency signal substantially in the X-band between a second high frequency transmitting antenna and a second high frequency receiving antenna.

11. A method as recited in claim 10 wherein said mixed fluids are water and oil.

12. The method as recited in claim 11 further comprising the steps of:
measuring a phase shift and attenuation of said low frequency signal;
measuring a phase shift and attenuation of said first high frequency signal;
measuring an attenuation of said second high frequency signal;
calculating a value of an X-band complex dielectric constant of fluid along a wall of the container from said phase shift and attenuation of said low frequency signal;
calculating a value of an S-band complex dielectric constant of said fluid along said wall from said phase shift and attenuation of said first high frequency signal;
calculating a volume fraction of water of said fluid along said wall;
calculating a correction factor to a mixing law;
calculating a conductivity of said water;
calculating a value of an S-band complex dielectric constant of fluid within said container; and
calculating a bulk volume fraction water in said container.

* * * * *